United States Patent [19]

Ringlien

[11] Patent Number: 5,233,186
[45] Date of Patent: Aug. 3, 1993

[54] INSPECTION OF TRANSPARENT CONTAINERS WITH OPPOSING REFLECTION MEANS

[75] Inventor: James A. Ringlien, Maumee, Ohio

[73] Assignee: Owens-Brockway Glass Container Inc., Toledo, Ohio

[21] Appl. No.: 901,009

[22] Filed: Jun. 19, 1992

[51] Int. Cl.$^5$ .............................................. G01N 9/04
[52] U.S. Cl. .................................. 250/223 B; 356/240
[58] Field of Search ............... 250/223 R, 223 B, 571, 250/572; 356/239, 240

[56] References Cited

U.S. PATENT DOCUMENTS

| | | |
|---|---|---|
| 2,429,066 | 10/1947 | Kuehni . |
| 3,533,704 | 10/1970 | Krenmayr . |
| 3,932,763 | 1/1976 | Weinstein ...................... 250/223 B |
| 4,207,467 | 6/1980 | Doyle . |
| 4,403,858 | 9/1983 | Yoshida . |
| 4,455,086 | 6/1984 | West et al. . |
| 4,601,395 | 7/1986 | Juvinall et al. . |
| 4,610,542 | 9/1986 | Ringlien . |
| 4,758,084 | 7/1988 | Tokumi et al. . |
| 4,775,889 | 10/1988 | Yoshida . |
| 4,863,268 | 9/1989 | Clarke et al. . |
| 4,920,385 | 4/1990 | Clarke et al. . |
| 4,959,538 | 9/1990 | Swart . |
| 5,041,726 | 8/1991 | Chang et al. . |
| 5,045,688 | 9/1991 | Domenico et al. . |
| 5,071,127 | 12/1991 | Bromley et al. . |
| 5,072,107 | 12/1991 | Apter . |

*Primary Examiner*—David C. Nelms

[57] ABSTRACT

Apparatus for detecting commercial variations in transparent containers such as glass bottles that includes a conveyor for directing containers along a path through an inspection station, and a light source disposed on one side of the path for directing light energy through a container at the inspection station. A light sensing camera is positioned on the same side of the conveyor path, and a retroreflector is positioned on the opposing side of the conveyor path opposite the light source and camera for reflecting light energy transmitted from the source through a container at the station back through the container onto the camera. Commercial variations are detected as a function of variations in intensity of light energy received at the camera.

10 Claims, 1 Drawing Sheet

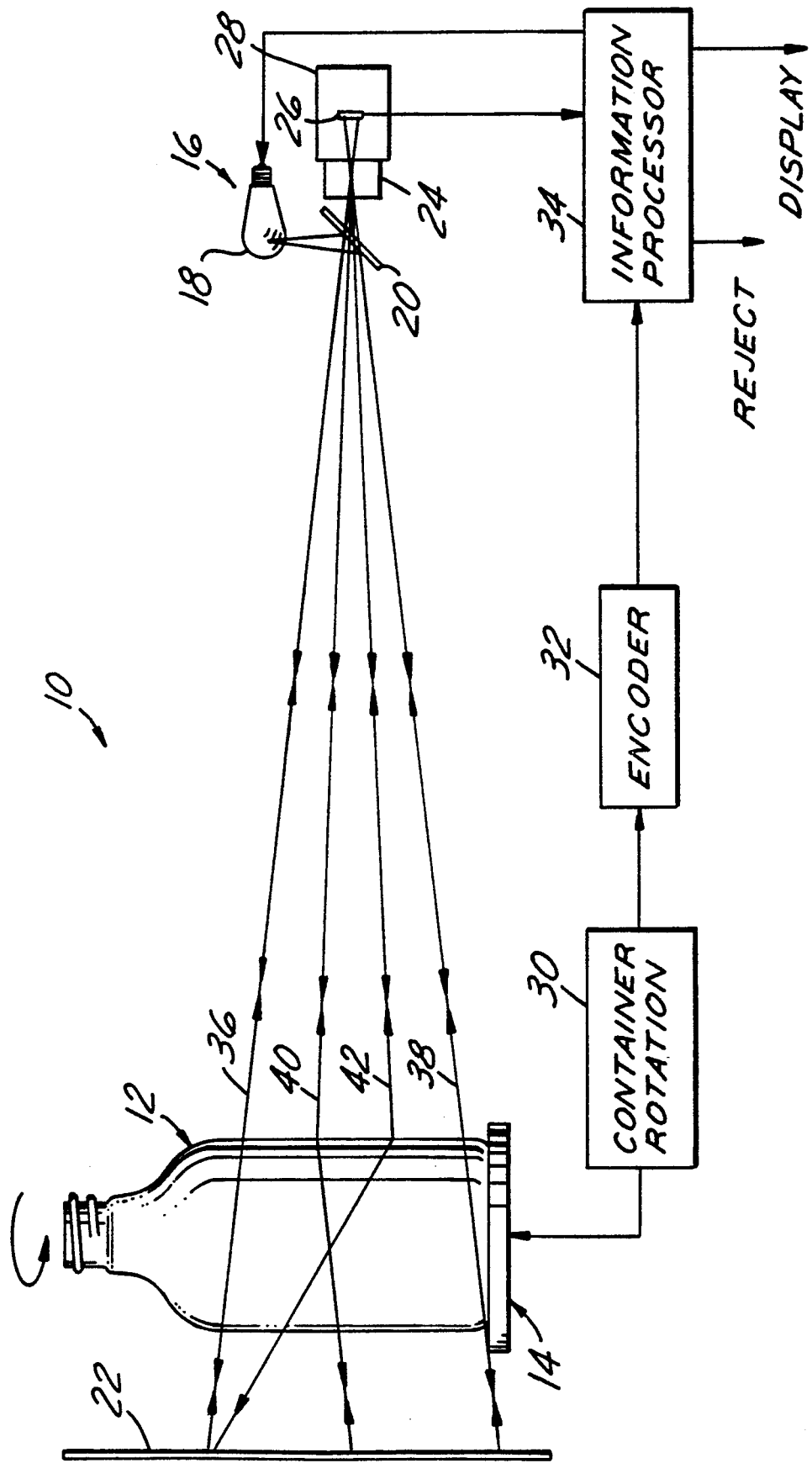

INSPECTION OF TRANSPARENT CONTAINERS WITH OPPOSING REFLECTION MEANS

The present invention is directed to inspection of transparent containers for commercial variations or defects that affect optical properties of the containers, and more particularly to an apparatus and method for enhanced detection of sharp-edge variations such as ribbon tears.

BACKGROUND AND OBJECTS OF THE INVENTION

In the manufacture of transparent containers such as glass bottles, various types of checks or defects may occur in the sidewalls, heels, bottoms, shoulders and/or necks of the containers. These checks or defects, termed "commercial variations" in the art, can affect commercial acceptability of the containers. The commercial variations may be opaque, such as stones, or may be refractive such as blisters, bubbles or tears.

It has heretofore been proposed to employ electro-optical inspection techniques for detecting commercial variations that affect optical properties of the containers. The basic principle is that a light source is positioned on one side of the container and a camera is positioned on the other. The light source may be configured to have an intensity that varies across one dimension of the source. Light rays normally travel from the source straight through the container and focused onto the camera, and are viewed at the camera at a given intensity. However, a refractive commercial variation bends the light ray as it travels through the container sidewall, so that the image projected onto the camera is of a different area of the light source. If such different area has a different intensity than the area normally imaged onto the camera, the camera can detect the refractive sidewall defect.

U.S. Pat. No. 4,610,542 discloses one technique for varying the effective intensity of the light source across the light source. An elongated filament lamp is positioned along the upper edge of a diffuser plate to produce an intensity gradient in the vertical direction across the light source. The upper area of the diffuser plate is brightest, the middle area has average brightness and the lower area is darkest. U.S. Pat. No. 4,601,395 discloses another technique in which a filter is placed across the light source diffuser screen to provide differing areas of effective light source intensity.

Although the systems disclosed in the noted patents, both of which are assigned to the assignee hereof, address problems theretofore extant in the art, further improvements remain desirable. In particular, container inspection systems of the character disclosed in the noted patents typically include a starwheel conveyor for conveying containers to and through the inspection station, and for holding the container stationary while it is rotated about its axis during the inspection process. The light source is positioned within the arcuate conveyor path —i.e., within the diameter of the starwheel—which creates space problems and necessitates use of a fairly large starwheel. Another difficulty with typical inspection systems heretofore proposed lies in the difficulty in detecting sharp-edged defects such as ribbon tears.

It is therefore a general object of the present invention to provide an inspection apparatus and method in which the major optical components—i.e., the light source and camera —are disposed on one side of the conveyor path, preferably externally of the arcuate path of a starwheel conveyor, which therefore forms a more simple and compact inspection system, and permits use of a smaller starwheel with reduced inertial and energy consumption. Another object of the present invention is to provide an apparatus and method for inspecting transparent containers of the described type that provide enhanced detection of sharp-edge commercial variations such as ribbon tears, as well as detection of other typical commercial variations such as stones, blisters, bubbles, lap marks and blowouts.

SUMMARY OF THE INVENTION

Apparatus for detecting commercial variations in transparent containers such as glass bottles in accordance with a presently preferred embodiment of the invention comprises a conveyor for directing containers along a path through an inspection station, and a light source disposed on one side of the path for directing light energy through a container at the inspection station. A light sensing camera is positioned on the same side of the conveyor path, and a reflector is positioned on the opposing side of the conveyor path opposite the light source and camera for reflecting onto the camera light energy transmitted from the source through a container at the station. Commercial variations are detected as a function of variations in light intensity received at the camera. In the preferred embodiment of the invention, the reflector comprises a retroreflector that reflects individual light rays back through the container along their illumination paths. Light rays that travel through the container without encountering a refractive variation, or encountering only a mild refractive variation, are incident on the camera to provide an overall bright image of the light source. However, light rays that encounter an opaque variation, or encounter a variation that strongly refracts the light ray, appear as a dark spot on the otherwise bright image.

In the preferred embodiment of the invention, the light source and sensor are respectively disposed to transmit and receive light energy along a common optical axis. A beam splitter is positioned on the optical axis for physically separating the light source and camera. The camera comprises a sensor array, either a linear array sensor or an area array sensor, that is scanned at increments of container rotation for developing a two-dimensional image of the container under inspection.

BRIEF DESCRIPTION OF THE DRAWING

The invention, together with additional objects, features and advantages thereof, will be best understood from the following description, the appended claims and the accompanying drawing. The sole drawing FIGURE is an electro-optical schematic diagram that illustrates a presently preferred embodiment of the invention.

DETAILED DESCRIPTION OF PREFERRED EMBODIMENT

The drawing illustrates an apparatus 10 for inspecting transparent containers 12 for commercial variations that affect the optical properties of the container. Apparatus 10 includes a conveyor 14, such as a starwheel conveyor of the type illustrated in above-noted U.S. Pat. No. 4,601,395, for conveying containers 12 along an arcuate path to and through an inspection station at which apparatus 10 is disposed. A light source 16 in the form of one or more light bulbs 18 is positioned to direct light energy onto a beam splitter 20, from which a portion of the light energy is reflected along an optical axis to and through the container 12 under inspection. A retroreflector 22 is positioned on the opposing side of container 12 to reflect the light energy incident thereon back through container 12 and along the same optical axis onto beam splitter 20. A portion of this reflected light energy is transmitted through beam splitter 20 to a lens system 24 having an entrance pupil disposed at the conjugate image of light source 16. Light energy is directed by system 24 onto an array sensor 26, which together with lens system 24 forms a light sensing camera 28.

Container 12 at the inspection station of apparatus 10 is coupled to a suitable device 30, such as a motor and drive wheel, for rotating container 12 about its axis during the inspection process. An encoder 32 is coupled to container rotation device 30 for providing a signal to an information processor 34 indicative of increments of container rotation, either directly as a function of angular increments of container rotation, or indirectly as a function of time increments during which container 12 is rotated at nominally constant angular velocity. Information processor 34 is coupled to camera 28 for scanning array sensor 26 at increments of container rotation, and thereby obtaining a two-dimensional image of the container and of light source 16 as viewed through the container. Information processor 34 provides outputs to a suitable display, and to a suitable mechanism for rejecting a container 12 in which commercial variations exceed a desirable level.

In operation, light energy from bulb 18 is reflected by beam splitter 20 through container 12, and then reflected by retroreflector 22 back through container 12 and beam splitter 20 through lens system 24 to camera array 26. Retroreflector 22, which may comprise a micro-corner cube sheet, a glass bead screen or a glass bead reflective paint on a substrate, is characterized by the fact that light energy incident thereon is nominally reflected back on itself along the path of incidence. Each light ray that travels through container 12 is refracted or bent according to the exact path that it travels as a function of sidewall geometry, as well as a function of any refractive variations that the ray encounters. Each ray (that is not blocked by an opaque variation) strikes reflector 22, and is nominally reflected back along its incoming path. Each ray then strikes the container, is refracted by the container along its original path of incidence, and then is directed onto camera sensor 26.

It has been found that light rays that encounter mild refraction due to container geometry, such as rays 36, 38 in the drawing, as well as light rays 40 that encounter only a mild refractive variation in the container, are directed by reflector 22 back along their paths of incidence to camera 28 to create a bright image of light source 16 at the camera. However, light rays 42 that encounter stronger refraction at the container, due to the refractive characteristics of unacceptable commercial variations, are not reflected by reflector 22 back along their paths of incidence, and thus appear as a dark spot in an otherwise bright image at camera 28. This is believed to be due to the fact that retroreflector 22 has a lower reflectivity for rays incident upon it at large angles from the normal angles of incidence. There is also a slight side shift and spreading of the returned rays so that they do not quite follow the exact path, which makes narrow edge variations such as ribbon tears appear wider at camera 28. Opaque variations, of course, appear as dark spots in an otherwise bright image since light rays cannot travel therethrough either to or from reflector 22.

It will therefore be apparent that apparatus 10 fully satisfies all of the objects and aims previously set forth. In particular, retroreflector 22 can be provided in the form of a very thin sheet, greatly increasing the amount of space available within the starwheel conveyor diameter and permitting use of smaller starwheel diameters. Furthermore, the inspection apparatus of the present invention has been found to operate well in detecting internal and external ribbon tears, stones, edges of blisters, lap marks and bad blowouts. Any location on the container where there is an abrupt thickness change appears dark at camera 28. Information processor 34 may employ any suitable technique for sensing dark spots in the camera image.

I claim:

1. Apparatus for detecting commercial variations in transparent containers that comprises:
   means for conveying containers along a path to an inspection station,
   a light source disposed on one side of said path for directing light energy through a container at said station,
   light sensing means positioned on the same said one side of said path,
   reflector means positioned on the other side of said path opposite said light source and light sensing means for reflecting light energy transmitted from said source through a container at said station onto said sensing means, and
   means for detecting commercial variations in the container at said station as a function of variations of light intensity received at said sensing means.

2. The apparatus set forth in claim 1 wherein said reflector means is disposed with respect to said source and said sensing means to receive light from said source transmitted through the container at said station and reflect such light back through the container to said sensing means.

3. The apparatus set forth in claim 2 wherein said reflector means comprises a retroreflector.

4. The apparatus set forth in claim 1 wherein said light source and said sensing means are respectively disposed to transmit and receive light energy along a common optical axis.

5. The apparatus set forth in claim 4 wherein said light source comprises a beam splitter disposed on said axis.

6. The apparatus set forth in claim 5 wherein said light sensing means includes a lens system disposed at the conjugate image of the light source.

7. The apparatus set forth in claim 1 wherein said conveying means comprises a starwheel conveyor for conveying the container along an arcuate path through said station, and wherein said reflector means is disposed within said arcuate path.

8. The apparatus set forth in claim 7 wherein said conveyor further comprises means for rotating the container about its axis at said inspection station.

9. The apparatus set forth in claim 1 wherein said light sensing means comprises an array sensor, and wherein said variations-detecting means comprises means for scanning said array sensor to develop a two-dimensional image of a portion of the container illuminated by said light source.

10. A method of inspecting transparent containers for commercial variations that affect optical properties of the containers, comprising the steps of:
   (a) directing light energy through a container such that individual light rays travel along paths that depend on optical properties of the container,
   (b) reflecting the light energy back through the container in such a way that individual light rays nominally travel in reverse direction along the same light paths, and
   (c) detecting commercial variations in the container as a function of intensity of light energy reflected back through the container.

* * * * *